US010070895B2

United States Patent
Barra et al.

(10) Patent No.: US 10,070,895 B2
(45) Date of Patent: Sep. 11, 2018

(54) DUAL TULIP ASSEMBLY

(71) Applicant: Amendia, Inc., Marietta, GA (US)

(72) Inventors: Kenneth Richard Barra, Acworth, GA (US); Karen Avanesov, Brooklyn, NY (US)

(73) Assignee: Amendia, Inc., Marietta, GA (US)

( * ) Notice: Subject to any disclaimer, the term of this patent is extended or adjusted under 35 U.S.C. 154(b) by 301 days.

(21) Appl. No.: 14/871,218

(22) Filed: Sep. 30, 2015

(65) Prior Publication Data

US 2017/0086895 A1   Mar. 30, 2017

(51) Int. Cl.
*A61B 17/70* (2006.01)
*A61B 17/86* (2006.01)
*A61B 17/00* (2006.01)

(52) U.S. Cl.
CPC ...... *A61B 17/7032* (2013.01); *A61B 17/8605* (2013.01); *A61B 2017/00526* (2013.01)

(58) Field of Classification Search
CPC .................. A61B 17/7032; A61B 17/7037
See application file for complete search history.

(56) References Cited

U.S. PATENT DOCUMENTS

| | | | |
|---|---|---|---|
| 6,562,038 B1 | 5/2003 | Morrison | |
| 6,676,661 B1 | 1/2004 | Martin et al. | |
| 7,799,059 B2 | 9/2010 | Aesculap ag | |
| 8,236,028 B2 | 8/2012 | Kalfas et al. | |
| 8,419,773 B2 | 4/2013 | Bidermann | |
| 8,834,541 B2 | 9/2014 | Vargas | |
| 8,998,961 B1 | 4/2015 | Ziemek et al. | |
| 9,510,867 B2 * | 12/2016 | Garamszegi | A61B 17/7032 |
| 9,615,867 B2 * | 4/2017 | Picetti | A61B 17/8605 |
| 2013/0085534 A1 | 4/2013 | Hainard et al. | |
| 2013/0274808 A1 | 10/2013 | Zimmer Spine | |
| 2013/0304128 A1 | 11/2013 | Lange et al. | |
| 2014/0088650 A1 | 3/2014 | Taddia et al. | |
| 2014/0163619 A1 * | 6/2014 | Harvey | A61B 17/7032 606/278 |

* cited by examiner

*Primary Examiner* — Andrew Yang
(74) *Attorney, Agent, or Firm* — David L. King

(57) ABSTRACT

A dual tulip assembly has a bone screw and a dual tulip. The dual tulip has a first tulip and a second tulip. Each first and second tulip has a slotted opening for receiving a rod. Each tulip is defined by a pair of sides, one side being common to both first and second tulips. On each side of each slotted opening, the sides have a proximal end with threads for engaging a set screw to secure a rod. The first tulip has an annular tapered distal end with an opening for receiving and securing the bone screw. The second tulip has a base forming a closed distal end. The bone screw has at least a partially hemispherical head. The bone screw has one of the following head shapes; at least partially a hemispherical or spherical head, or any other bulbous head. The dual tulip is a single piece structure.

16 Claims, 12 Drawing Sheets

DUAL TULIP ASSEMBLY

TECHNICAL FIELD

The present invention relates to an improved implant device for use in spinal surgical procedures most particularly, an improved tulip design.

BACKGROUND OF THE INVENTION

Bone anchor screws come in a variety of shapes and sizes. One of the more common styles has a polyaxial head that allows for the screw to enter the bone structure at an ideal or preferred inclination. To achieve this polyaxial inclination, the head has a shape configured to rotate about its lower external surface. This lower surface can be one of a number of shapes like conical or spherical or hemispherical. This ability is often used in devices having a modular head assembly.

The bone screw assembly generally includes a tulip. A tulip is a body structure having two opposing sides spaced by a slotted opening to receive a spinal rod. The tulip often employs internal threads to receive a rod locking set screw to anchor or fix the rod in the tulip. The lower portion of the tulip has an opening to receive the bone screw in a base seat. Often, the tulip can have a saddle that both supports the rod along an underside of the rod. The saddle having an upper recessed curvature into which the rod sits and a lower cup like opening to receive the top of the bone screw head. When the saddle and rod and set screw are tightened, the screw angle is fixed against the tulip seat.

Often, it is preferred that the bone screw is first placed securely in the bone structure leaving the head protruding above the bone surface. In this surgical procedure the tulip assembly must be adapted to fit down onto the projecting screw head. To accomplish this, the surgeon must push the tulip onto and over the screw head without a clear path of vision. Accordingly, the placement must be accomplished without any way of knowing if the tulip or other device is properly secured. Thereafter, the device is tightened to complete the assembly and the only way to insure the assembly is secure requires an upward pulling of the tightened assembly. This works well when fixation of two adjacent vertebrae is being performed and the length of the fixation rod is relatively short.

If, however, the span is long, as it is when three vertebrae segments are being fixed, this often requires the use of a bent rod or requires the surgeon to bend the rod to custom fit the patient.

The present invention solves this problem in a unique one piece structure that allows a second rod to be used in a tulip that is particularly crafted to accommodate two rods while employing a single bone screw in the assembly.

SUMMARY OF THE INVENTION

A dual tulip assembly has a bone screw and a dual tulip. The dual tulip has a first tulip and a second tulip. Each first and second tulip has a slotted opening for receiving a rod. Each tulip is defined by a pair of sides, one side being common to both first and second tulips. On each side of each slotted opening, the sides have a proximal end with threads for engaging a set screw to secure a rod. The first tulip has an annular tapered distal end with an opening for receiving and securing the bone screw. The second tulip has a base forming a closed distal end. The bone screw has at least a partially hemispherical head. The bone screw has one of the following head shapes; at least partially a hemispherical or spherical head, or any other bulbous head. The dual tulip is a single piece structure. The head of the bone screw has a driving feature for torsionally driving the screw into bone.

The slotted opening of the first tulip and the slotted opening of the second tulip each have a bottom being vertically aligned respectively. The second slotted opening is offset relative to the first slotted opening. Each slotted opening has a center plane, each first tulip and second tulip center plane is parallel relative to the other. The closed base of the second tulip is positioned above the distal end of the first tulip.

In one embodiment, the dual tulip assembly further may have a saddle being internal of the first tulip positioned in a recess inside the first tulip, the saddle having a proximal end for engaging a rod and a distal end for receiving the bone screw. The saddle has an exterior surface positioned between the ends. The exterior surface is sized to move axially inside the first tulip aligned by a pair of complimentary convex arcuate projections. Each projection is configured to enter one of said opposing slots. The saddle has a plurality of arcuate fingers positioned to create a bulbous exterior shape with an interior receiving chamber complimentarily shaped relative to the head of the bone screw. The arcuate fingers are separated by slots extending from near the proximal end through the distal end in an initial pre-loaded position. The plurality of arcuate fingers collectively are larger in diameter than the tapered end annular opening of the first tulip. Upon insertion of the dual tulip, the first tulip moves over the head of the bone screw. The saddle moves proximally over the head simultaneously causing the arcuate fingers to flex and move past a maximum diameter of the head holding the head in the complimentary shaped interior receiving chamber of the first tulip. Upon tightening the rod by the set screw, the plurality of arcuate fingers are compressed about the head of the bone screw by the distal tapered end thereby fixing the bone screw into the first tulip. The saddle has each finger having an arcuate shape with an inwardly positioned chamfered end for sliding on the surface of the head of the bone screw thereby flexing the plurality of arcuate fingers. The recess of the first tulip has a conical surface tapering inward distally, the conical surface compresses the plurality of arcuate fingers when tightening the set screw. The relaxed outer diameter of the bulbous exterior of the saddle is larger than a distal opening of the first tulip. The saddle has at least six or more fingers separated by slots. An inner surface of the saddle along an inner surface of the plurality of fingers forms the complimentary head receiving chamber in a hemispherical or at least partial hemispherical shape sized to pass over and past the maximum diameter of the head of the bone screw. Each finger has a length, width or thickness sufficiently compliant to flexure or deflect inward or outward to expand or contract upon assembly and tightening.

A method of assembling a dual tulip assembly has the step of providing a dual tulip assembly having a first and a second tulip; and positioning a saddle inside the first tulip retained in a recess. The method of assembling a dual tulip assembly also includes the step of positioning the saddle inside the tulip to flex or deflect to an expanded condition as positioned over the head of a bone screw. The method of assembling a dual tulip assembly also includes the steps of installing a first rod in said first tulip and securing with a set screw, and installing a second rod in said second tulip and securing with a set screw.

BRIEF DESCRIPTION OF THE DRAWINGS

The invention will be described by way of example and with reference to the accompanying drawings in which.

DETAILED DESCRIPTION OF THE INVENTION

Figure 1:
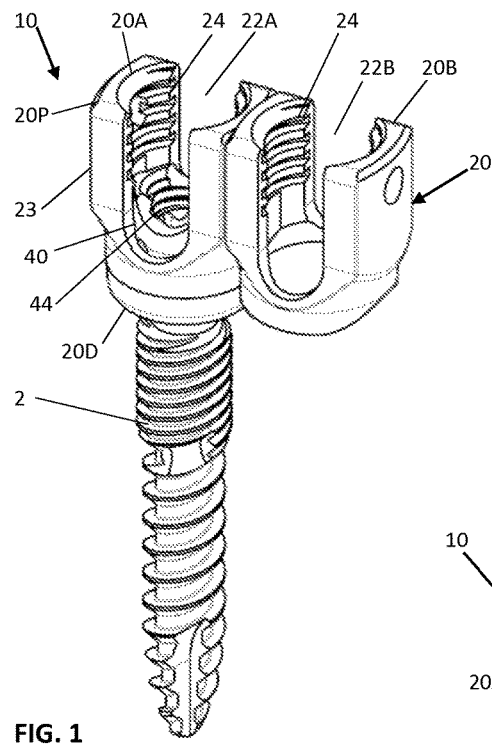
FIG. 1 is a plan view of the dual tulip assembly of the present invention.
Figure 2:
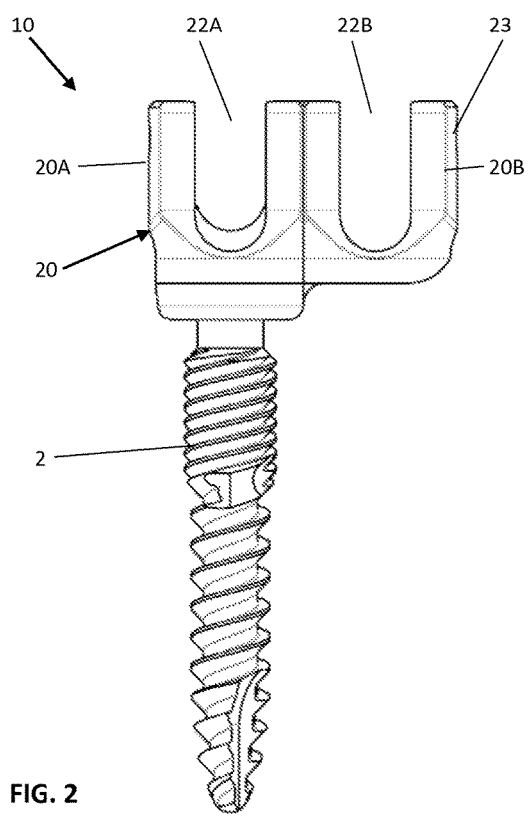
FIG. 2 is a side view of the dual tulip assembly of FIG. 1.

With reference to FIGS. 1-5, a dual tulip assembly 10 is illustrated. As shown in FIG. 1, the assembly 10 has a dual tulip 20, a bone screw 2 and an optional seat or saddle 40. As illustrated, the dual tulip 20 has a first tulip 20A and a second tulip 20B. Each tulip has a slotted opening 22A, 22B respectively. The proximal end 20P of the dual tulip 20 has threads 24 that extend inwardly for receiving a set screw to lock a rod into position in both the first tulip 20A and the second tulip 20B respectively. As shown in FIG. 2, the dual tulip 20 has the slots 22A and 22B shown approximately the same in vertical height relative to the screw 2, but offset laterally one relative to the other. Both slots are defined by sides 23. The sides 23 define the slotted openings 22A and 22B. The middle side 23 is threaded on both walls to make the first and second tulips conjoined at the center and divides the dual tulip 20 into a first tulip 20A and a second tulip 20B. As shown, the dual tulip 20 is manufactured in a single piece of material.

When two rods 60 are positioned, one in each slotted opening 22A and 22B, the rods 60 can be aligned parallel, but slightly offset or can even be inclined slightly relative to the other rod 60. This ability to incline the rods allows the dual tulip 20 to be positioned between two standard single tulip assemblies and allow two straight rods 60 to be oriented angularly relative to the other at a desired inclination spanning several vertebrae. This allows the surgeon to achieve a custom rod sizing without resorting to bending rods. It also allows the rod length to be less critical as slight oversizing in length is absorbed at the dual tulip assembly 10.

Figure 3:
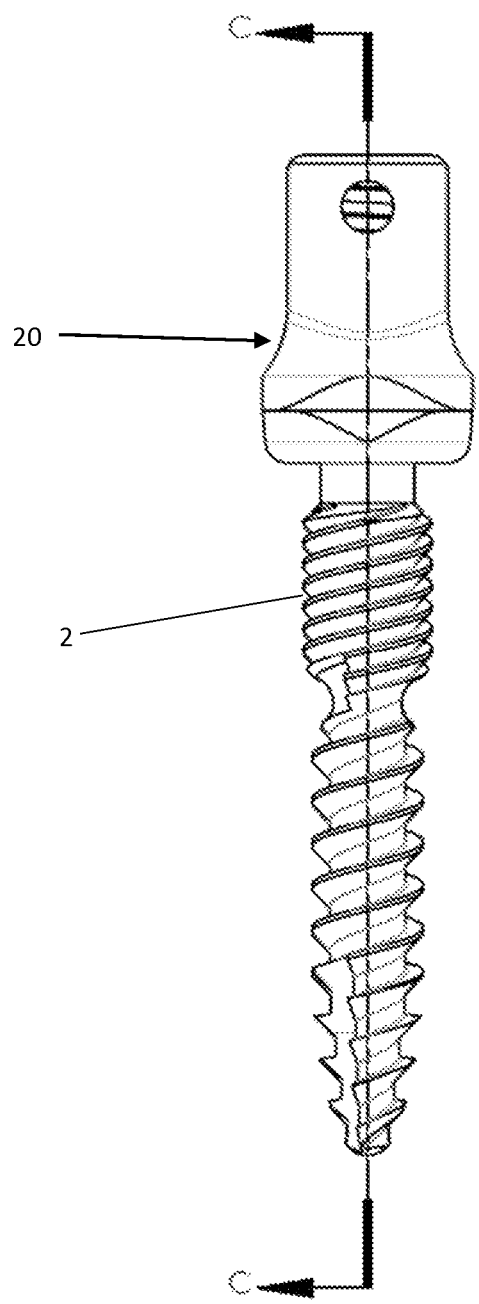
FIG. 3 is a side end view of the dual tulip assembly of FIG. 1.
Figure 4:
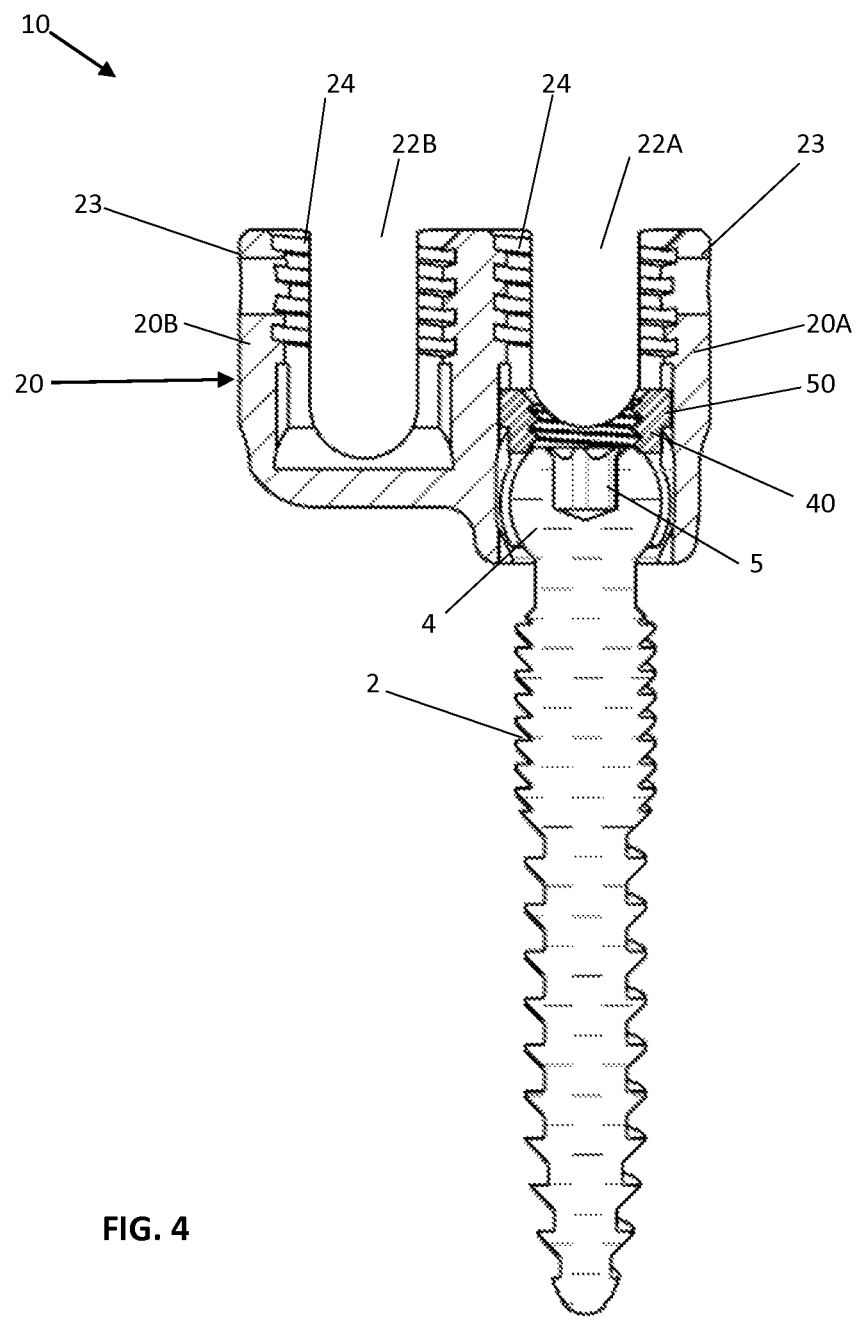
FIG. 4 is a cross sectional view taken along lines C-C of FIG. 3.
Figure 5:
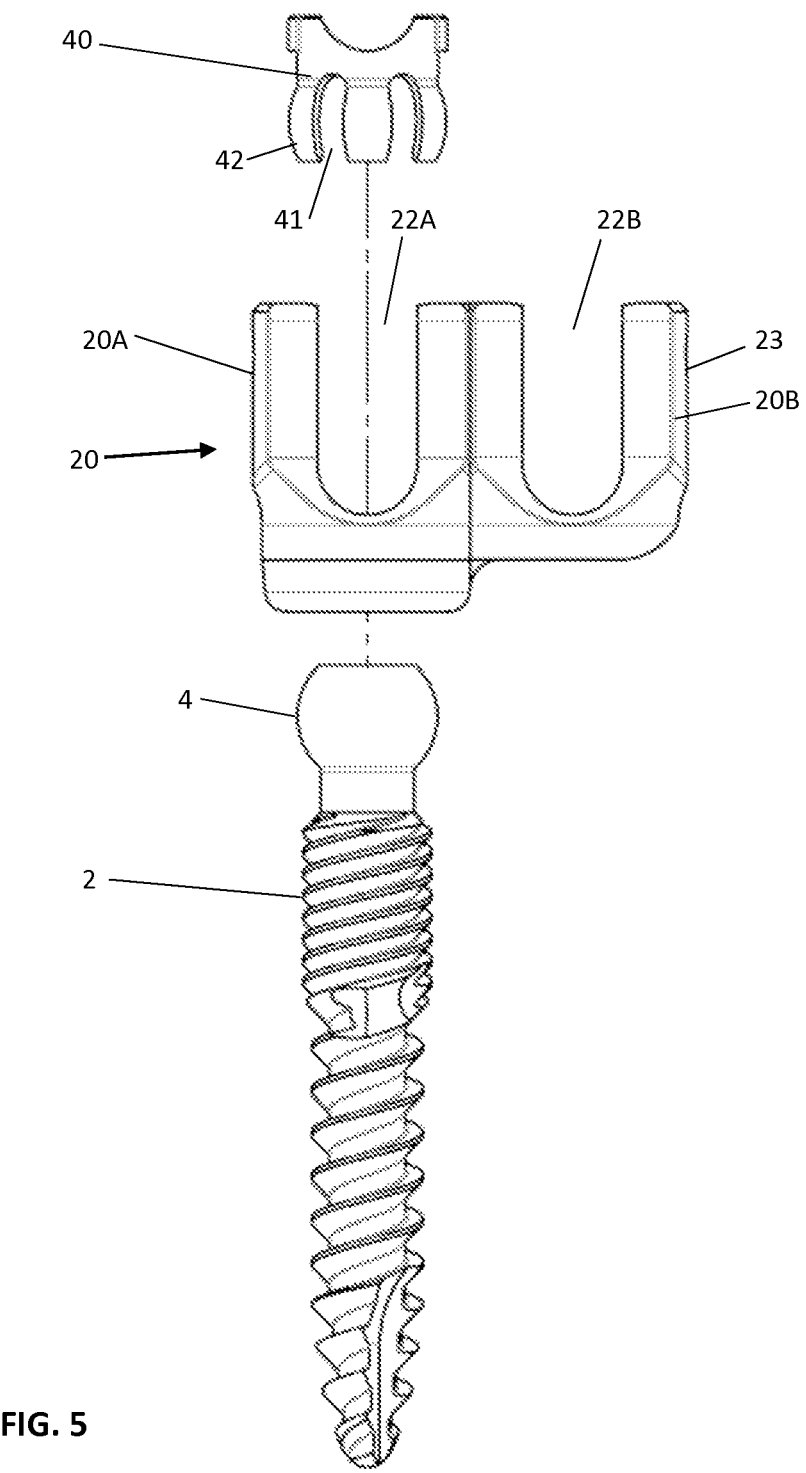
FIG. 5 is an exploded view of the dual tulip assembly.
Figure 6A:
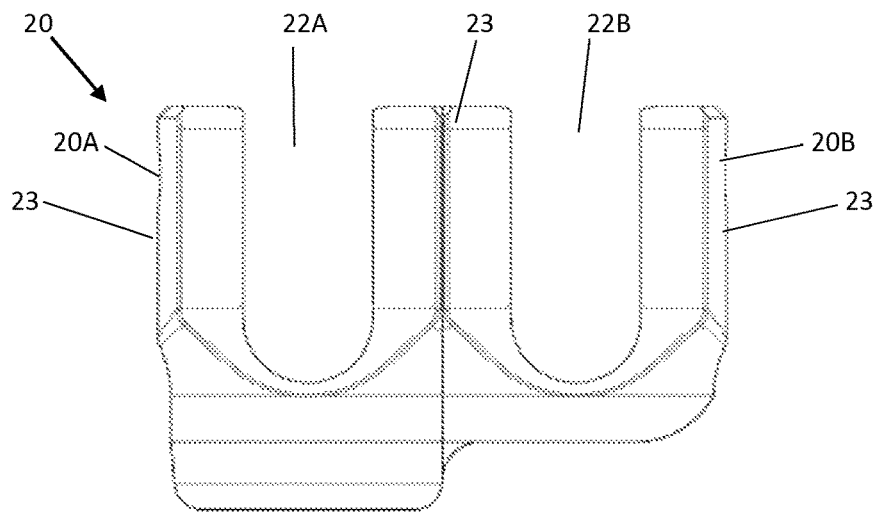
FIG. 6A is a side view of the dual tulip of the present invention.
Figure 6B:
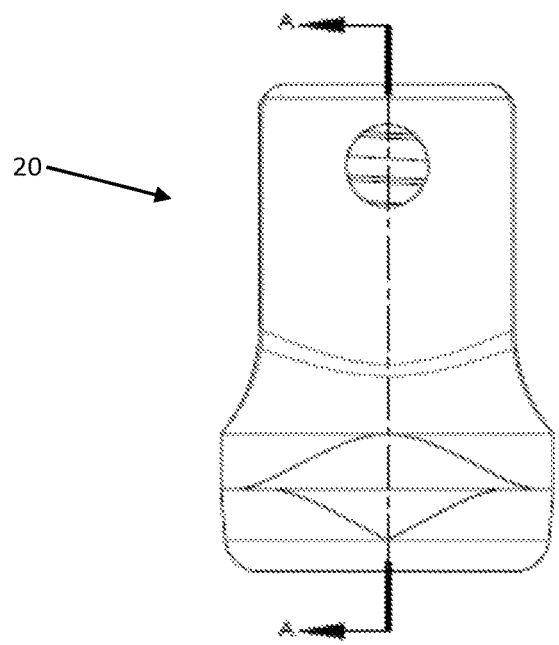
FIG. 6B is a side end view of the dual tulip.
Figure 6C:
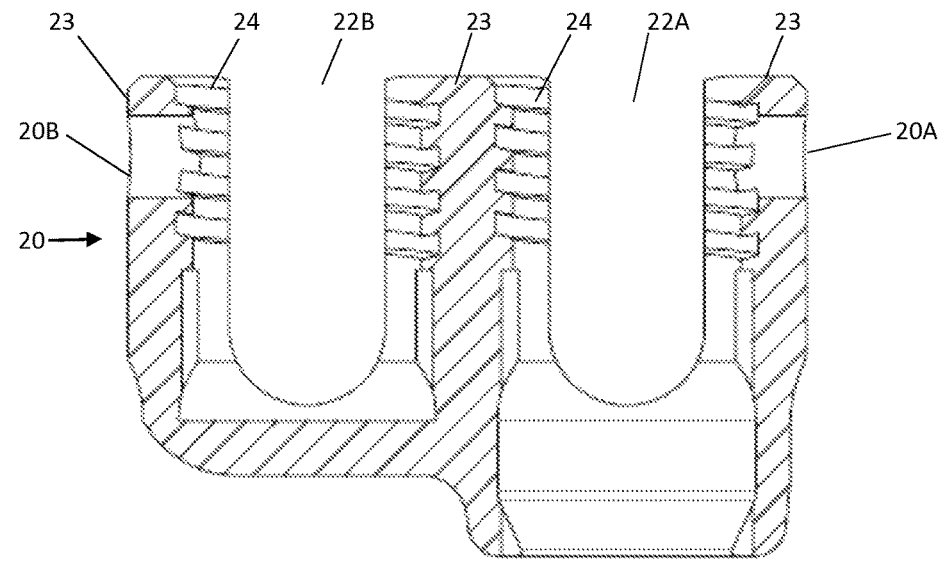
FIG. 6C is a cross sectional view taken along lines A-A of FIG. 6B.
Figure 6D:
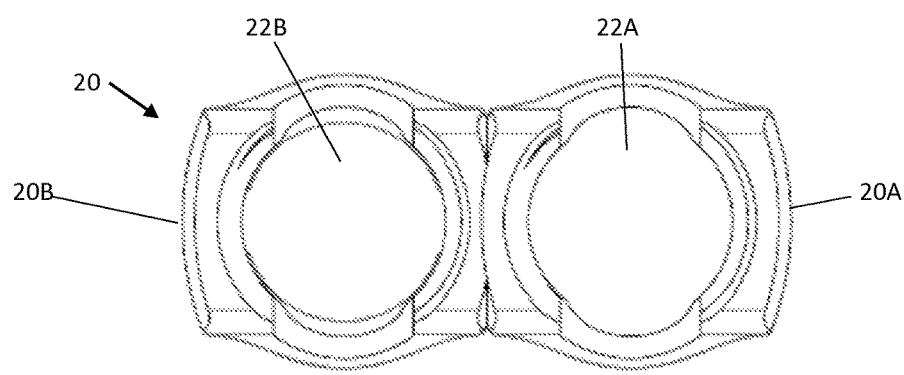
FIG. 6D is a top view of the dual tulip.

FIG. 4 shows a cross-sectional view along lines C-C taken from FIG. 3. As shown, the bone screw 2 is fully seated in the first tulip 20A and held by the saddle 40. In the adjoining tulip 20B, the bottom or base of the structure is shown in a closed position whereas the first tulip 20A has the distal end 20D open to allow the head 4 of the bone screw 2 to pass inwardly. This is best illustrated in FIG. 5, where the bone screw 2 is shown below the dual tulip 20 and the saddle 40 is shown above the dual tulip 20 as illustrated in the exploded view.

With reference to FIGS. 6A-6D, the dual tulip 20 is shown in greater detail. As shown in the cross sectional view of 6C, the threads 24 at the proximal end 20P are designed to receive a set screw. When the set screw is in position it can hold the rod in the slotted opening 22A or 22B. As further illustrated, the bottom or base of the second tulip 20B is closed and positioned above the distal opening 20D of the first tulip 20A. By elevating the closed base of the second tulip 20B allows the dual tulip 20 to be easily attached to a bone screw 2 even when the bone screw 2 is already positioned in a vertebral body. This enables the assembly 10 to be snap-fit together in a modular fit allowing the dual tulip 20 to be placed onto a bone screw 2 in the first tulip 20A and held by the saddle 40 which will be explained in detail.

Figure 7:
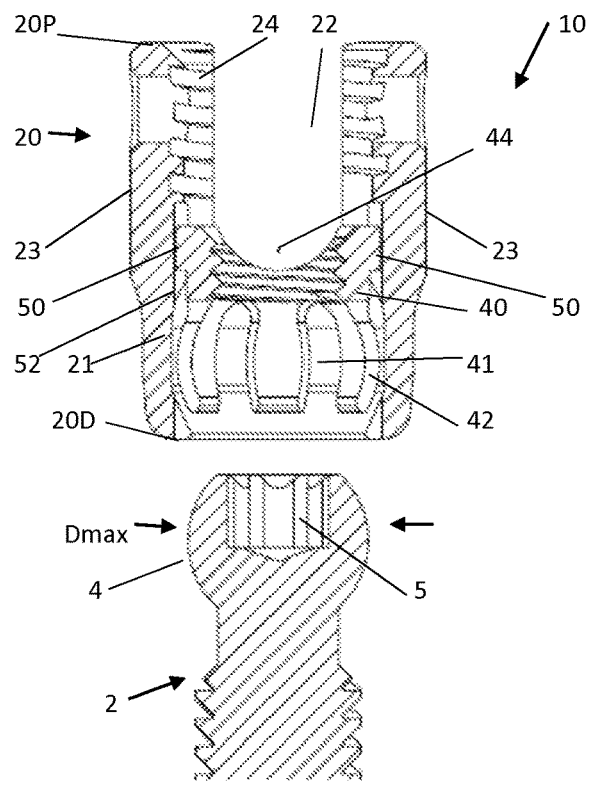
FIG. 7 is a cross-sectional view of a tulip and saddle assembly above a head portion of a bone screw.

With reference to FIGS. 5, 7-10, in FIG. 7, a cross-sectional view of the first tulip with saddle is shown with the bone screw 2 not attached below the assembly is illustrated. In FIG. 1, a tulip 20 is shown in a plan view. The first tulip 20A has a slotted opening 22A defined by opposed sides 23 to receive a rod and has internal threads 24 into which a set screw can be inserted that allow a rod to be positioned into the tulip 20 on assembly.

With reference to FIG. 7, a cross-sectional view of the assembly 10 is illustrated, internal of the first tulip 20A is a recess. The proximal end 20P is shown, below that internal of the first tulip 20A are the threads 24 for receiving the set screw illustrated later in FIGS. 11 and 12. Below the threads 24 is a recess portion 21 the tulip 20 with a saddle 40 illustrated inside the recess 21. As shown, the saddle 40 also has a concavity 44 for receiving a rod, this concavity 44 is in the form of a partially circular arc configured to the shape of the rod which it will receive and hold tightly upon final assembly. The saddle 40 has a proximal end for rod receiving and a distal end for receiving the head 4 of bone screw 2. The bone screw 2 is partially shown below the assembly of the tulip 20 and the saddle 40.

Figure 8:
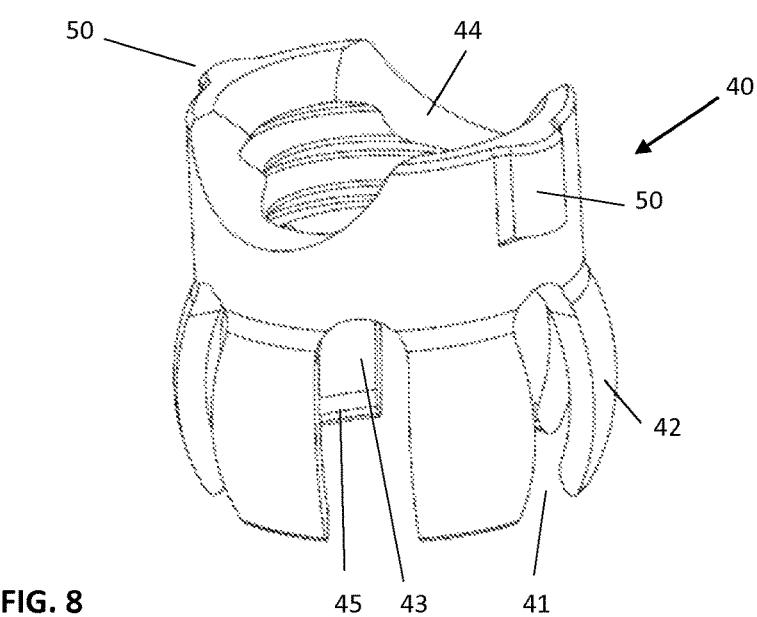
FIG. 8 is a perspective view of the saddle of the present invention.

As further illustrated in FIG. 8, with reference to the saddle 40, a plurality of fingers 42 are shown defined by the slots 41 cut in near proximity to the recess 44 for receiving the rod near the proximal end and extending inwardly towards a distal end. Near the distal end, the fingers 42 have a slight chamfer 45 with an inwardly sloping configuration. The combination of fingers 42 and slots 41, as shown, form a somewhat hemispherical bulbous surface extending toward the distal end or opening. On the exterior surface of the saddle 40 at the proximal end is shown a pair of opposed arcuate convex projections 50 extending partially toward the fingers 42. These projections 50 fix the alignment of the saddle 40 in the tulip 20. As shown in FIG. 7, the first tulip 20A has a pair of opposed arcuate concave slots 52 for receiving the projections 50. The slots 52 being closely sized to receive the projections 50 fix the saddle 40 and first tulip 20A so the rod 60 receiving openings or slotted opening 22 and recess 44 are fixed in alignment.

Figure 9:
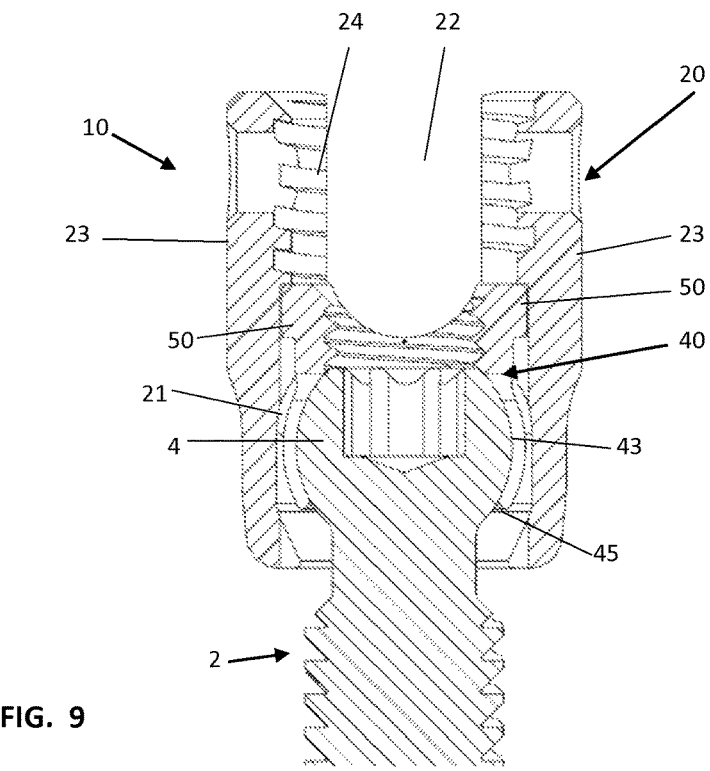
FIG. 9 is a cross-sectional view of the tulip and saddle assembly shown positioned onto the head of a bone screw in a loose or untightened condition.

With reference to FIG. 9, when the saddle 40 and first tulip 20A of the dual tulip assembly 10 are positioned over the head 4 of the bone screw 2, the fingers 42 are configured to have an internal surface or cavity 43, shown in FIG. 8, that matches or is complimentary to the surface of the head 4 of the bone screw 2. As illustrated, the head 4 of the bone screw 2 is either at least partially or fully hemispherical and the saddle 40 has the complimentary internal surface or cavity 43 adapted to receive the head 4 of this bone screw 2 in such a fashion that when the bone screw 2 is entered into the saddle 40, the fingers 42 will receive the head 4 of the bone screw 2. The fingers 42 are designed with a sufficient length, thickness and width that they will deflect or flexure outwardly or inwardly. On assembly, the fingers 42 move slightly outwardly as the chamfers 45 slide over the surface of the head 4 past the maximum diameter Dmax of the head 4 of the bone screw 2 and slide past the maximum diameter Dmax until fully seated inside the saddle 40 as illustrated in FIGS. 4 and 9. When this occurs, the saddle 40 and the head 4 of the bone screw 2 are still able to move proximally or distally because the dual tulip assembly 10 has not been tightened and the fingers 42 will hold the head 4 loosely so the saddle 40 can move angularly about head 4.

Figure 10:
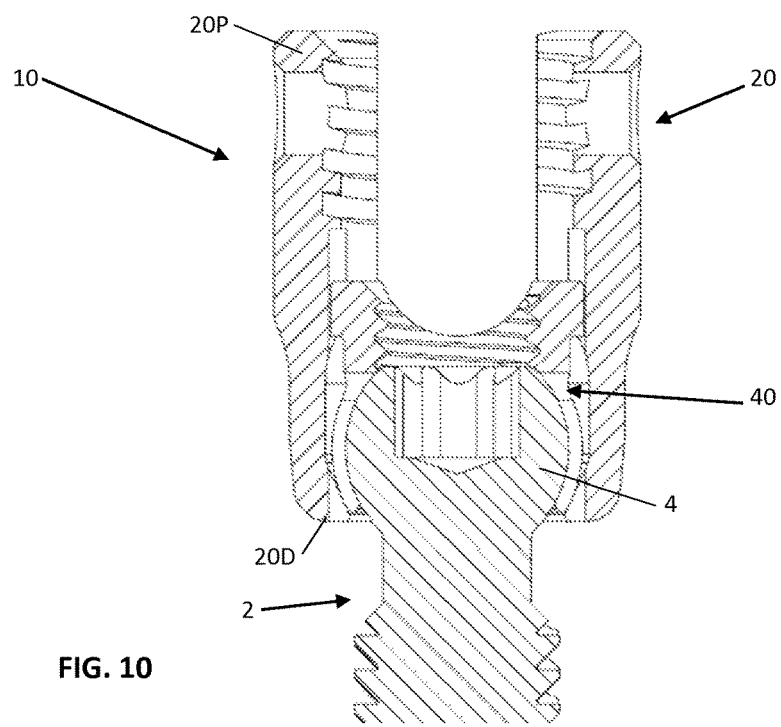
FIG. 10 is a view showing the saddle moved to the tightened positioned.

With further reference to FIG. 10, the saddle 40 when tightened, will move directionally towards a distal end 20D of the tulip 20. The distal end 20D of the tulip 20 has a conical shape in the recess such that it tapers inwardly, this conical shape is designed to be larger than the maximum diameter of the head 4 of the bone screw 2 so the head 4 of the bone screw 2 can freely pass into the tulip 20, but on entry will engage the saddle 40 adjacent the interior surface 43 of the fingers 42, as previously mentioned. As the saddle 40 is tightened, it moves toward the distal end 20D, the fingers 42 near the distal end of the saddle 40 mate with the conical surface of the tulip 20 and compress inwardly tightening the fingers 42 about the head 4 of the bone screw 2. The fingers 42 deflect inwardly compressing and tightening and due to the fact that they are below the maximum diameter of the bone screw 2, when this occurs the bone screw 2 is rigidly and securely held by the tightened saddle 40.

Figure 11:
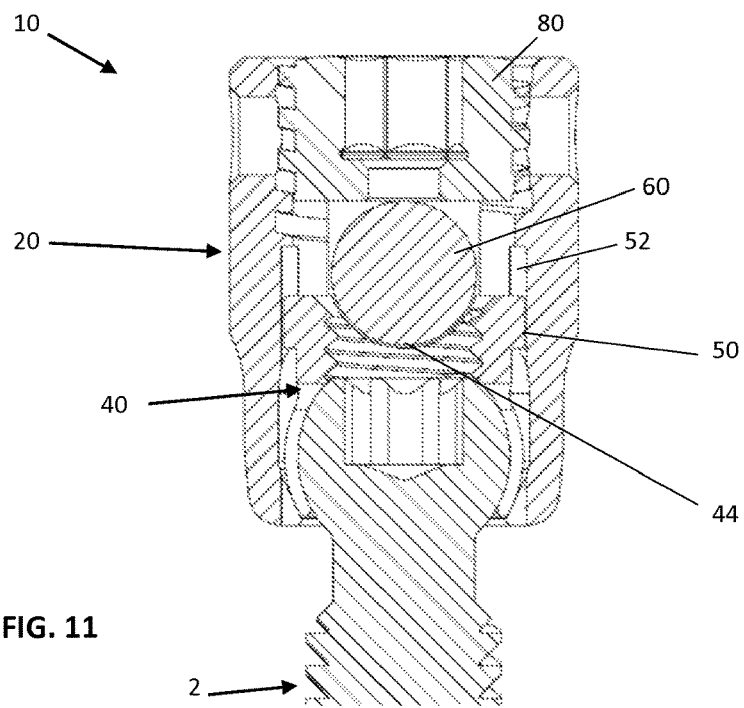
FIG. 11 is a cross-sectional assembly plan view of the tulip, saddle assembly tightened about the head of a bone screw showing the rod held in the saddle and fixed by a set screw; the rod and set screw when so assembled, drive the saddle distally compressing the fingers.
Figure 12:
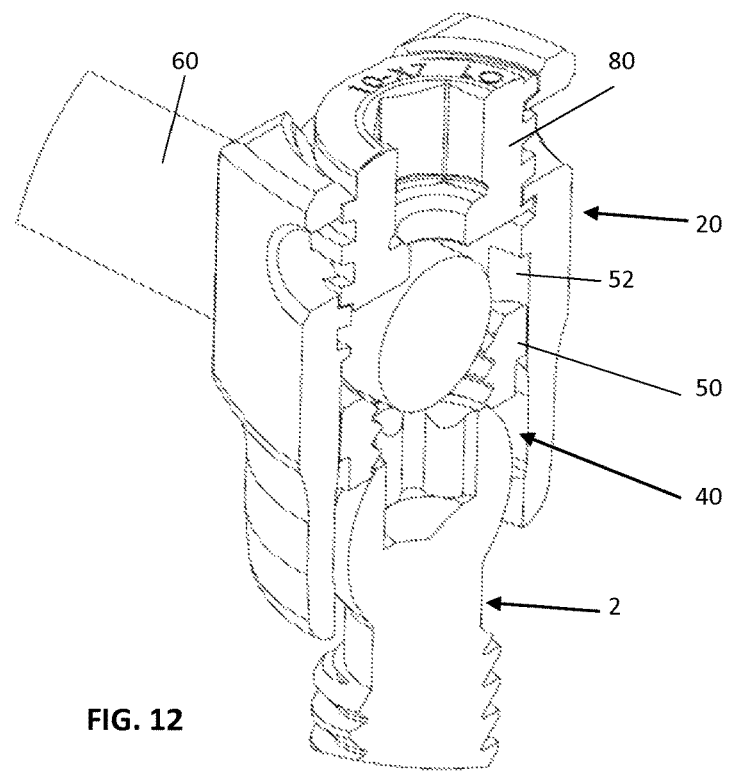
FIG. 12 is a perspective view of the view of FIG. 6.

With reference to FIGS. 11 and 12, in order to accomplish this initial tightening of the tulip 20 and saddle 40 assembly 10 against the hemispherical or at least partially hemispherical head 4 of the bone screw 2, there is illustrated a rod 60 and set screw 80. The rod 60 is shown fitting into the proximal end of the saddle 40 and tulip 20 through the slotted opening 22A and resting on the concavity 44 complimentary to the rod 60 so that it is positioned in such a fashion that it is supported inside the tulip 20 by at least the saddle 40 along this concavity 44 of the saddle 40. A set screw 80 is then inserted into the assembly 10 and tightens against the rod 60, as the rod 60 and set screw 80 are driven toward the distal end 20D the saddle 40 moves distally toward the conical distal end 20D of the tulip 20 and the fingers 42 are compressed tightly against the head 4 of the bone screw 2 past the maximum diameter of the head 4 of the bone screw 2. This creates a secure assembly and fixes both the angularity of the tulip 20 relative to the bone screw 2 and fixes the tulip 20 assembly 10 firmly onto the head 4 of the bone screw 2. Upon tightening, the assembly is now complete.

As shown, the dual tulip 20 and saddle 40 assembly 10 can be positioned in such a way that they fit onto a bone screw 2, which has been driven into the bone by the use of a driver tool inserted into the tool drive opening 5, that can already be pre-positioned in a pedicle or other bone structure of a patient. In this fashion, the tulip 20 and saddle 40 combined dual tulip assembly 10 are configured to be moved over and above the bone screw 2 already positioned in the bone, fit onto the head 4 of the bone screw 2, adjusted for angularity due to the fact that the saddle 40 is not tightened and therefore the first tulip 20A and saddle 40 subassembly 10 are free to move in any axial direction about the hemispherical or partial hemispherical portion of the head 4 of the bone screw 2. The advantage of the present invention is that the angularity and fixing of the dual tulip assembly 10 on the bone screw 2 to the head 4 is all accomplished at one element, the saddle 40 as the rod 60 and set screw 80 are assembled and tightened. The movement of the saddle 40 having a plurality of flexible, compressible and deflectable fingers 42 having an inner surface 41 complimentary to the head 4 of the screw 2, but past the maximum diameter Dmax ensures that upon compression, the entire assembly 10 is fixed so that the dual tulip 20 cannot be pulled or slipped off the bone screw 2 once affixed. This creates a tremendous advantage over prior art devices requiring additional components. The present invention achieves this locking of the dual tulip assembly 10 to the head 4 of the bone screw 2 in a rather simple and reliable manner.

Figure 13:
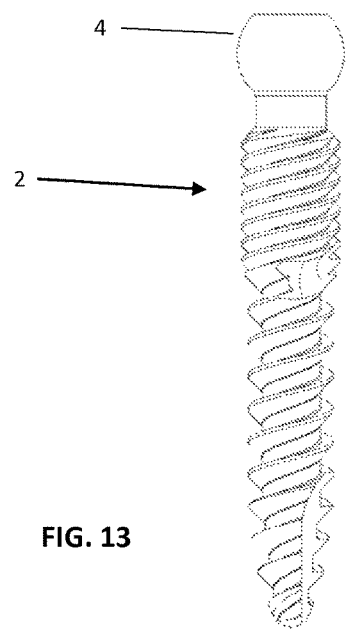
FIG. 13 is a view of an exemplary pedicle or bone screw used with the present invention.
Figure 14:
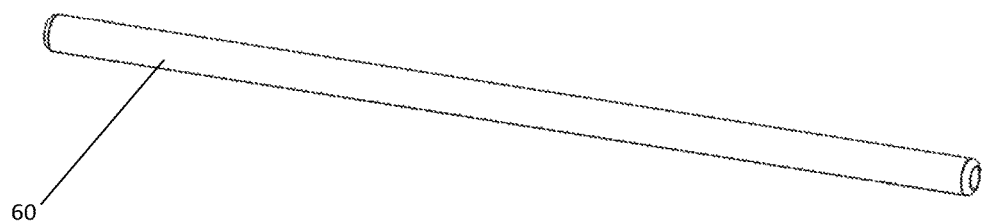
FIG. 14 is a view of the rod used with the present invention.
Figure 15:
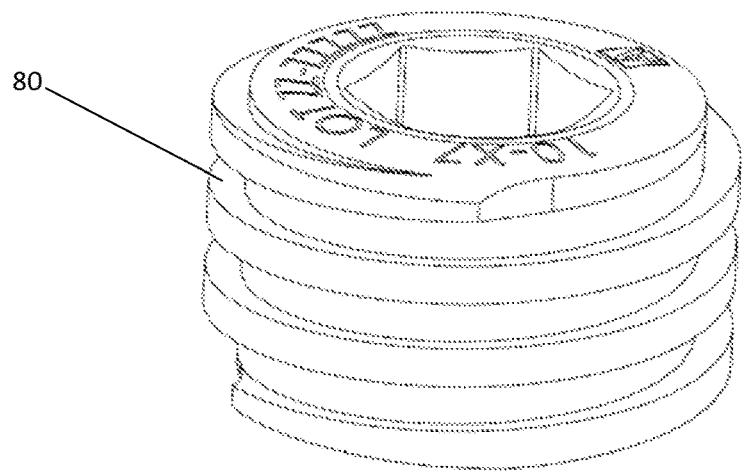
FIG. 15 is a view of the set screw used with the present invention.

With reference to FIGS. 13-15, FIG. 13 is a view of an exemplary pedicle or bone screw 2 used with the present invention. FIG. 14 is a view of the rod 60 and FIG. 15 is a view of the set screw 80 used with the present invention.

Figure 16:
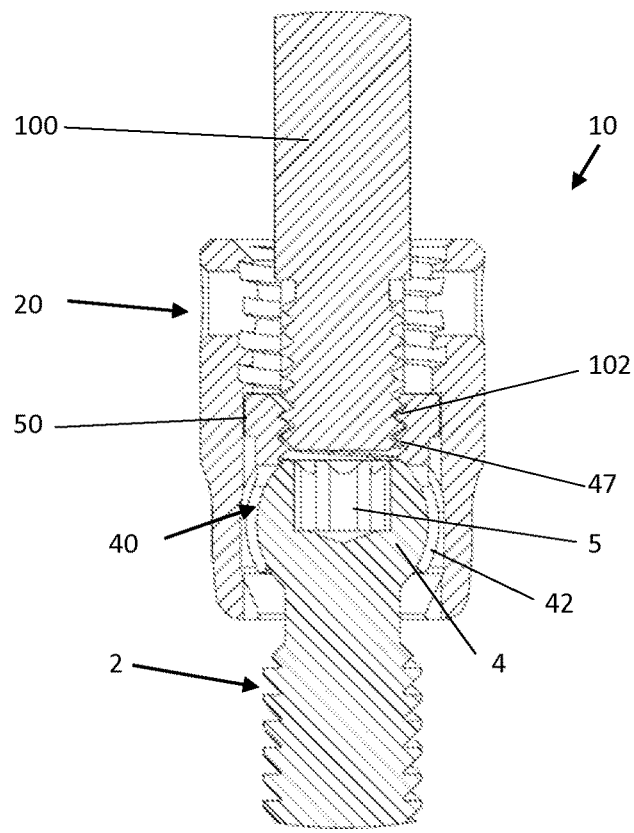
FIG. 16 shows how a release tool engages the saddle of the present invention.
Figure 17:
FIG. 17 shows a plan view of the release tool.

With reference to FIGS. 16 and 17, a release tool 100 can be provided. As shown in FIG. 16, when the tulip 20 and saddle 40 are snapped over the head 4 of the bone screw 2, a release tool 100 with external threads 102 can thread into the threads 47 to move back over the maximum diameter Dmax of the head 4 to allow the saddle 40 to unlock from the screw 2. Thereafter, the tulip 20 with saddle 40 can be released from the screw head 4.

As shown, the present invention can be sized to allow its use in various surgical procedures including the cervical and previous thoracic, lumbar, sacral, and iliac applications. In the cervical spine, the bone screws are not called pedicle screws, but instead are commonly called lateral mass screws. The dual tulip may have applications for all these regions. The dual tulip is especially useful in the iliac connection.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. A modular dual tulip comprising:
   a saddle affixed to the modular dual tulip, the saddle having a rod receiving concavity for holding a rod, the saddle having threads configured to receive a release tool;
   a single piece of material forming the dual tulip, the dual tulip having a first tulip and a second tulip, each first and second tulip having a slotted opening for receiving a rod wherein a second slotted opening being offset relative to a first slotted opening, each slotted opening having a center plane, each first tulip and second tulip center plane being parallel relative to the other, each tulip being defined by a pair of sides, one side being common to both first and second tulips, on each side of each slotted opening the sides having a proximal end with threads for engaging a set screw to secure a rod, the first tulip has an annular tapered distal end with an opening sized to allow the saddle with a concavity to receive a head of a bone screw to pass inwardly into a recess portion of the first tulip for receiving and securing a bone screw, the recess portion has a pair of arcuate concave slots spaced from the first slotted opening configured to receive a pair of opposed convex projections on an exterior surface of the saddle, the projections extending from a proximal end of the saddle toward a distal end, the opposed arcuate concave slots of the recess being closely sized to receive the convex projections of the saddle to fix circumferentially the rod receiving concavity of the saddle and first slotted opening of the first tulip are in fixed alignment about said center plane of the first tulip along with the head of the bone screw, the second tulip has a base forming a closed distal end, wherein the dual tulip is a single piece structure, and wherein when the tulip and saddle are snapped over the head of the bone screw, the saddle and tulip lock onto the head, thereafter to remove the saddle, a release tool with external threads can thread into the threads of the saddle to back over a maximum diameter $D_{max}$ of the head to allow the saddle to unlock from the screw releasing the tulip with the saddle from the screw head.

2. The dual tulip of claim 1 wherein the slotted opening of the first tulip and the slotted opening of the second tulip each have a bottom being vertically aligned respectively.

3. The dual tulip of claim 1 wherein the closed base of the second tulip is positioned above the distal end of the first tulip.

4. A modular dual tulip assembly comprising:
a single piece structure forming the dual tulip, the dual tulip having a first tulip and a second tulip, each first and second tulip having a slotted opening for receiving a rod wherein a second slotted opening being offset relative to a first slotted opening, each slotted opening having a center plane, each first tulip and second tulip center plane being parallel relative to the other, each tulip being defined by a pair of sides, one side being common to both first and second tulips, on each side of each slotted opening the sides having a proximal end with threads for engaging a set screw to secure a rod, the first tulip has an annular tapered distal end with an opening for receiving and securing a bone screw, the second tulip has a base forming a closed distal end;
a saddle being internal of the tulip positioned in a recess inside the first tulip, the saddle having a proximal end having a concavity for holding and for engaging a rod and a distal end for receiving head of the bone screw, the saddle having threads configured to receive a release tool;
wherein the saddle having an exterior surface positioned between the ends, the exterior surface being sized to move axially inside a recess portion of the first tulip from the distal opening aligned by a pair of opposed arcuate slots spaced from the first slotted opening in the first tulip for receiving a pair of complimentary convex arcuate projections on the exterior surface of the saddle, each arcuate projection extending from the proximal end of the saddle toward the distal end configured to enter one of said opposing arcuate slots to fix circumferentially the rod receiving concavity of the saddle and first slotted opening of the first tulip are in fixed alignment about said center plane of the first tulip along with the head of the bone screw, the saddle having a plurality of arcuate fingers positioned to create a bulbous exterior shape with an interior receiving chamber complimentarily shaped relative to a head of a bone screw, the arcuate fingers separated by slots extending from near the proximal end through the distal end in an initial pre-loaded position, the plurality of arcuate fingers collectively being larger in diameter than the tapered end annular opening of the first tulip; and
wherein upon insertion of the first tulip and the circumferentially fixed and aligned saddle over the head of the bone screw, the saddle axially moves proximally over the head simultaneously causing the arcuate fingers to flex and move past a maximum diameter of the head, locking onto while loosely holding the head in the complimentary shaped interior receiving chamber and upon tightening the rod by the set screw, the plurality of arcuate fingers are compressed about the head of the bone screw by the distal tapered end thereby fixing the bone screw into the tulip, and wherein when the tulip and saddle are snapped over the head of the bone screw, the saddle and tulip lock onto the head, thereafter to remove the saddle, a release tool with external threads can thread into the threads of the saddle to back over a maximum diameter $D_{max}$ of the head to allow the saddle to unlock from the screw releasing the tulip with the saddle from the screw head.

5. The dual tulip assembly of claim 4 wherein the slotted opening of the first tulip and the slotted opening of the second tulip each have a bottom being vertically aligned respectively.

6. The dual tulip assembly of claim 4 wherein the closed base of the second tulip is positioned above the distal end of the first tulip.

7. The dual tulip assembly of claim 4 further comprises a bone screw.

8. The dual tulip assembly of claim 7 wherein the bone screw has at least a partially hemispherical head.

9. The dual tulip assembly of claim 8 wherein the saddle has each finger having an arcuate shape with an inwardly positioned chamfered end for sliding on the surface of the head of the bone screw thereby flexing the plurality of arcuate fingers.

10. The dual tulip assembly of claim 8 wherein the recess of the tulip has a conical surface tapering inward distally, the conical surface compresses the plurality of arcuate fingers when tightening the set screw.

11. The dual tulip assembly of claim 8 wherein the relaxed outer diameter of the bulbous exterior of the saddle is larger than a distal opening of the tulip.

12. The dual tulip assembly of claim 8 wherein the saddle has at least six or more fingers separated by slots.

13. The dual tulip assembly of claim 12 wherein an inner surface of the saddle along an inner surface of the plurality of fingers forms the complimentary head receiving chamber in a hemispherical or at least partial hemispherical shape sized to pass over and past the maximum diameter of the head of the bone screw.

14. The dual tulip assembly of claim 8 wherein each finger has a length, width or thickness sufficiently compliant to flexure or deflect inward or outward to expand or contract upon assembly and tightening.

15. The dual tulip assembly of claim 4 wherein the bone screw has one of the following head shapes; at least partially a hemispherical or spherical head, or any other bulbous head.

16. The dual tulip assembly of claim 4 wherein the head of the bone screw has a driving feature for torsionally driving the screw into bone.

* * * * *